United States Patent [19]

Dormandy, Jr. et al.

[11] Patent Number: 4,544,371

[45] Date of Patent: Oct. 1, 1985

[54] IMPLANTABLE METERED DOSE DRUG DELIVERY SYSTEM

[75] Inventors: Ray H. Dormandy, Jr., Goleta; Frederick L. Coe, Santa Barbara, both of Calif.

[73] Assignee: American Hospital Supply Corporation, Evanston, Ill.

[21] Appl. No.: 433,053

[22] Filed: Oct. 5, 1982

[51] Int. Cl.$^4$ .............................................. A61M 5/00
[52] U.S. Cl. .................................... 604/891; 604/246; 604/185
[58] Field of Search ............................... 604/890–891, 604/175, 185, 9, 93, 246; 128/1 R

[56] References Cited

U.S. PATENT DOCUMENTS 3,827,439  8/1974  Schulte et al. ...................... 604/185
4,013,074  3/1977  Siposs ................................. 604/891

Primary Examiner—C. Fred Rosenbaum
Assistant Examiner—Harrie S. Samaras
Attorney, Agent, or Firm—Roger A. Williams

[57] ABSTRACT

An implantable metered dose drug delivery system is disclosed which comprises implantable components including an injection site, reservoir, metering valve and delivery catheter, all of which are interconnected through suitable tubing. The metering valve has a domed body constructed of a resilient elastomeric material with a fluid-flow passageway extending therethrough and opening into a chamber within the domed body. A valve is positioned within an outlet leading from the chamber, which valve is opened by exerting an external pressure on the domed body to first collapse and occlude the fluid-flow passageway and then open the valve to permit medication within the chamber to flow through the outlet. Upon release of the external pressure, the fluid-flow passageway opens and reduced pressure in the chamber draws additional fluid through the passageway to fill the chamber.

23 Claims, 8 Drawing Figures

IMPLANTABLE METERED DOSE DRUG DELIVERY SYSTEM

BACKGROUND OF THE INVENTION

The invention herein is directed to an implantable metered dose drug delivery system. More particularly, the implantable metered dose drug delivery system herein has utility in the treatment of pain associated with or brought about due to cancer and other similar diseases.

Many diseases and ailments which plague mankind also have associated with them pain and discomfort. For example, the presence of cancer can cause severe and intense pain for considerable time. Such pain is a great discomfort to the individual who must learn to tolerate the pain or take medication for alleviating the pain. In many instances, the administering of medication is unpleasant and can cause discomfort or undesirable side effects to other systems of the individual. In some instances, the medication is of short duration and thereby only of temporary relief to the individual. The systemic narcotic dose required for alleviation of severe cancer pain often leaves the patient drowsy and inactive. However, animal and human studies have shown that focal application of morphine in the spinal epidural or subarachnoid space results in pain abatement without depression of the central nervous system. Poletti et al describe a system for the focal application of morphine in J. Neurosurg., Vol. 55, pp. 581–584, October 1981.

It would be desirable to have an implantable drug delivery system which could be implanted in the body of an individual which could meter out the proper dosage of pain reliever to the spinal epidural or subarachnoid space to provide pain abatement. It would be desirable to have such a system which could be activated by the patient without the need to continually visit a physician.

SUMMARY OF THE INVENTION

The invention herein is directed to an implantable metered dose drug delivery system. The implantable metered dose drug delivery system herein comprises an injection site which provides for administering additional medicine or pain reliever to the system. A reservoir for the medication or pain reliever is provided which is connected through a suitable catheter or conduit to the injection site. A metering valve is connected to the reservoir through a suitable conduit. The metering valve provides unit dose delivery of the medication to the individual. The metering valve can be manually activated to provide the necessary unit dose delivery as the medication is needed. The metering valve is designed such that it can be actuated by the individual or by the physician. The metering valve is connected through a conduit to an anti-reflux catheter placed in the spinal epidural or subarachnoid space. Between the metering valve and anti-reflux catheter another valve may be placed in the system. Such a valve can be a positive off valve to insure that the medication flow path from the metering valve to the anti-reflux catheter is closed. All components of the system are constructed of biocompatible material so that they can be readily implanted in the body.

The metering valve comprises a resilient dome-shaped body having a restricted input fluid-flow passage extending through the resilient dome body and into a chamber within the resilient body of the metering valve. The inner chamber of the metering valve is designed to provide a volume substantially equivalent to the desired dose of the medication to be administered. The metering valve is provided with an outlet having at least one deformable-type valve. The valve is positioned in the outlet and within the resilient body of the metering valve such that the valve opens when an external pressure is applied to the domed body of the valve.

An anti-reflux or a one-way valve can also be positioned in the outlet conduit leading from the metering valve, which one-way valve permits fluid flow outwardly of the metering valve.

BRIEF DESCRIPTION OF THE DRAWINGS

The implantable metered dose drug delivery system herein will be better understood with regard to the following detailed description and accompanying drawings wherein.

DETAILED DESCRIPTION

Figure 1:
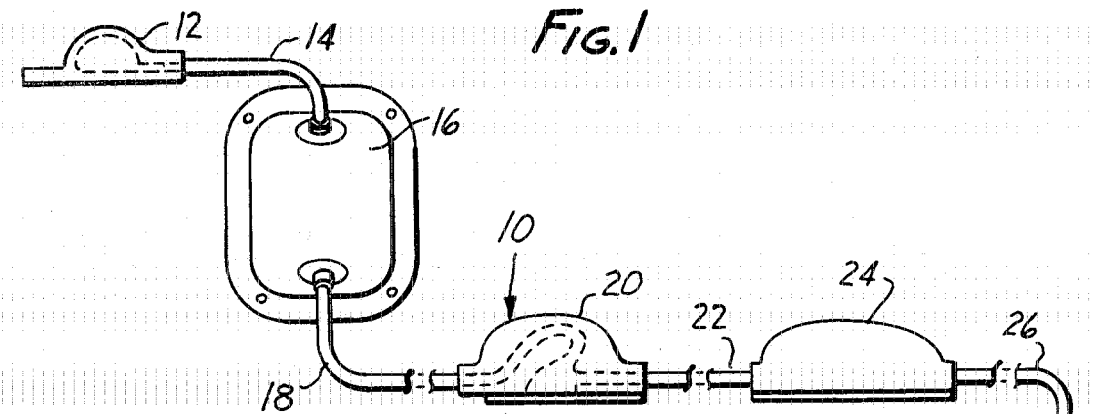
FIG. 1 is a schematic illustration of the components of the system herein.
Figure 2:
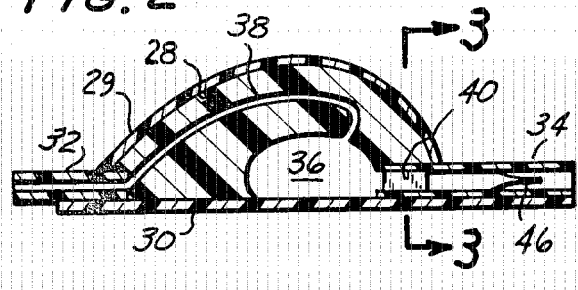
FIG. 2 is a side elevational view in cross section of a preferred embodiment of the metering valve having utility in the system herein.
Figure 3:
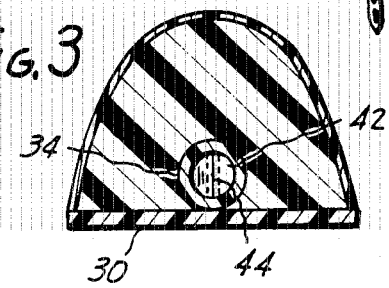
FIG. 3 is a cross-sectional, slightly enlarged, view of the metering valve in FIG. 2 taken along lines 3—3.

With reference to FIG. 1, the implantable metered dose drug delivery system 10 is illustrated by its individual components. The system comprises an implantable injection site 12 which can be constructed of any biocompatible material. Suitable implantable injection sites for use in the system herein are disclosed in U.S. Pat. No. 4,190,040 to Schulte titled "Resealable Puncture Housing for Surgical Implantation" and U.S. Pat. No. 4,217,889 to Radovan and Schulte titled "Flap Development Device and Method of Progressively Increasing Skin Area," the entire disclosures of which are herein incorporated by reference.

Basically, the injection site comprises a puncturable, resealable housing having an inner chamber into which medication can be delivered through a hypodermic syringe. The hypodermic syringe is used to puncture through the housing and into the inner chamber of the housing. The housing body of the injection site can be of a self-sealing material or can contain and confine a sealing material in a laminate-type structure.

In the preferred embodiment herein, the injection site is constructed of silicone which is biocompatible with the human body.

The injection site is connected through a conduit or catheter 14 to a reservoir 16. The reservoir is constructed of a biocompatible material, such as silicone, and has a chamber for holding the medication to be administered. The reservoir can be of any desired size which can be determined by the treatment to be administered to the patient. For example, in some techniques of cancer treatment the reservoir can be from 100 to 300 milliliters in volume. Greater volumes or lesser volumes can be used depending upon the treatment to be administered.

The connection of the injection site to the reservoir permits the introduction of additional medication to the reservoir when the medication in the reservoir is depleted. In addition, the injection site provides a method for administering other medication to the system if desired.

The reservoir is provided with an outlet and catheter or conduit 18 connected to the outlet. The catheter or conduit 18 is also connected to a metering valve 20.

The metering valve 20 functions as a dosing reservoir to hold the desired dose of medication to be administered. In addition, the metering valve functions as a pump for delivering the measured dose of medication. The metering valve also functions as a valve to prevent the early or inadvertent release of the medication and to prevent the backflow of liquid from the site of administration into the metering valve and from the metering valve back into the reservoir. The structure of the metering valve will be described hereinafter with regard to FIGS. 2–6.

Connected to the outlet of the metering valve is a catheter or conduit 22 which can lead directly to an anti-reflux catheter 26 or can be connected to the anti-reflux catheter 26 through a positive off valve 24. The positive off valve when used in the system provides a safeguard to prevent the inadvertent delivery of medication or the accidental overdose of medication. In addition, the positive off valve can provide a check to prevent backflow of fluid into the metering valve.

The anti-reflux catheter can be a peritoneal anti-reflux catheter or similar type catheter. The catheter can have openings which are maintained open or which open under pressure of the fluid within the catheter. For example, the openings can be slit openings which open upon a sufficient pressure being exerted by the fluid within the catheter.

A working embodiment of the metering valve 20 is illustrated in FIGS. 2–5. The metering valve comprises a domed-shaped body 28 having a base 30 that is relatively flat so as to be readily implantable and positionable within the body. The base need not be flat, but can be contoured so as to fit the contour of any desired portion of the body.

The body of the metering valve is domed-shaped and constructed of a resilient material which is biocompatible with the human body. For example, silicone rubber is an acceptable biocompatible resilient material. However, other elastomers can be used to construct the dome.

In a working embodiment constructed as depicted in FIG. 1, the body comprised a silicone rubber having a durometer of 20 to 50 (Shore A). A 20 to 50 durometer body for the metering valve provides sufficient elasticity to perform the functions desirable of the body of the metering valve herein. It is preferred that an outer layer 29 of the body of the metering valve have a relatively higher durometer than the major portion of the domed body; i.e., greater than 50. Such an arrangement can be made by constructing a dome of a suitable durometer, then filling the dome with elastomer of the preferred, more resilient durometer. Another method of forming such a body is to provide additional curing of the elastomer along its outer edge so as to provide a higher durometer skin or film covering.

The body of the metering valve is provided with an inlet passage or inlet conduit 32 and and outlet passage or outlet conduit 34. The outlet conduit 34 opens into a chamber 36 disposed within the body of the metering valve. The chamber 36 functions as a dose reservoir for holding a specific volume of medication to be administered. The volume of the chamber 36 can be varied depending upon the end use of the metering valve and the medication to be administered by the particular metering valve. For example, the chamber can have a volume from about 1/10 to 1/20 cc for delivering such an amount of medication.

Figure 4:
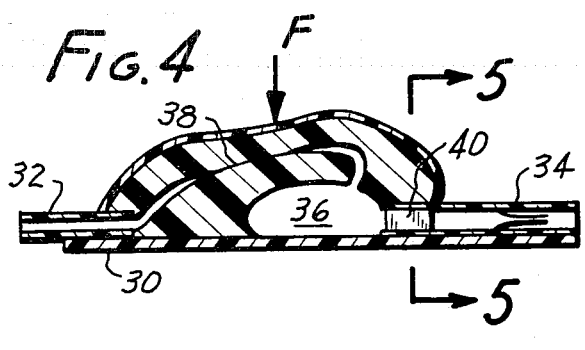
FIG. 4 is a side elevational view in cross section of the metering valve of FIG. 2 illustrating the operation of the metering valve.

The chamber 36 is in fluid communication with the inlet conduit 32 through a fluid passageway 38. The fluid passageway 38 extends from the inlet conduit 32 through the resilient body of the metering valve. Preferably, the fluid passageway 38 extends generally centrally of the metering valve and opens into the chamber along an upper wall of the chamber. That is, the fluid passageway is positioned superiorly of the chamber. The fluid passageway can have any convenient cross section and in the preferred working embodiment the fluid passageway has a cross section that is oval in shape with a width greater than its height. The height was 0.020 inches and the width was 0.100 inches. The fluid passageway is of sufficiently small size so that it can be collapsed upon the exertion of an external pressure against a superior portion of the metering valve. That is, upon exertion of such an external force, the fluid passageway collapses, thereby occluding the passageway to fluid flow. Such a position is illustrated in FIG. 4 wherein the domed body of the metering valve is shown distorted by a force F and the fluid passageway 38 collapsed.

Within the outlet conduit 34 is a first valve 40. The first valve 40 is a valve which remains closed under normal conditions, but which opens upon a force being exerted against the domed body of the metering valve. Suitable valves for the first valve 40 include slit valves and miter valves. A miter valve is the preferred valve and when such a miter valve is utilized, it is preferably positioned such that the slit opening 44 between the valve flaps 42 extends in a generally vertical direction with regard to the base. That is, at about a right angle to the general plane of the base. The orientation of the first valve can be seen by referring to FIGS. 2 and 3.

The outlet conduit 34 is constructed of a biocompatible material, such as a silicone rubber, which has a durometer greater than the durometer of the resilient body portion of the metering valve. For example, the outlet conduit can have a durometer of 50 or greater. The outlet conduit includes a portion which extends into the body of the metering valve so that forces exerted on the body are translated to the outlet conduit.

The first valve 40 is positioned such that the slit opening is adjacent the chamber within the body of the metering valve. That is, if the first valve is a miter valve, it is positioned in the outlet conduit as if the fluid flow were to be into the chamber from the outlet. Extending around the flaps 42 of the first valve is additional elastomer having a relatively low durometer. The elastomer is preferably the same elastomer that is used to construct the body of the metering valve; i.e., an elastomer having a durometer of 20–50. The elastomer positioned around the valve flaps 42 tends to maintain the first valve in a closed position for preventing fluid flow through the first valve and outlet conduit. It is desirable to prevent unwanted fluid flow from the chamber 36 to avoid unnecessarily overdosing the patient with the medication.

There can also be positioned within the outlet conduit 34 a one-way valve 46. The one-way valve 46 is positioned in the outlet conduit to provide fluid flow outwardly of the metering valve and to prevent fluid flow through the outlet conduit back into the chamber of the metering valve. Any suitable one-way valve can be utilized, such as the miter valve shown in the drawings. The one-way valve 46 need not be present in the metering valve itself, but can be in a separate component of the overall system as is shown in FIG. 1. That is, a positive off valve 24 can be utilized to prevent backflow of fluid through the outlet conduit.

In operation, the metering valve is operated by exerting an external pressure on the resilient dome body 28. As shown in FIG. 4, the initial pressure F exerted on the resilient dome of the body 28 collapses the fluid passageway 38. Upon collapse of the fluid passageway 38, fluid flow from the chamber 36 is prevented through such passageway.

Figure 5:
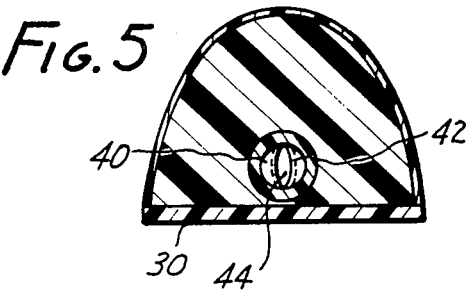
FIG. 5 is a cross-sectional, slightly enlarged, view of the metering valve in FIG. 4 taken along lines 5—5.

As the external pressure is increased on the resilient dome body of the metering valve, the first valve 40 begins to experience radially outwardly directed forces and concomitantly a force generally axially with the slit opening 44. Such forces tend to open the first valve as is shown in FIG. 5. The radially outwardly directed forces are brought about by a combination of the relatively greater durometer of the outlet conduit compared to the body of the metering valve and the resilient elastomer material packed around the valve flaps 42. Such forces open the valve as is shown in FIG. 5. The continued application of pressure on the dome forces the medication in chamber 36 to flow out of the chamber and through the outlet conduit 34. In this manner, the medication is administered to the patient in which the system is implanted.

Upon release of the pressure, the first valve closes and the fluid passageway 38 is again opened. The reduced pressure within the chamber 36 draws additional medication from the reservoir through the inlet conduit and fluid passageway into the chamber to again charge the chamber with the appropriate dosage of medication. As can be appreciated, the structure of the metering valve prevents inadvertent drug delivery as intermittent or transient forces on the domed body merely close the fluid passageway 38 without opening the first valve.

Again with reference to FIG. 1, a positive off valve 24 can be inserted in the system and connected to the metering valve 20. The positive off valve can be any convenient one-way valve which can prevent backflow of fluid from the anti-reflux catheter 26 into the metering valve 20. The positive off valve can be constructed so as to be opened by manually manipulating the valve or by fluid pressure within the system.

Figure 7:
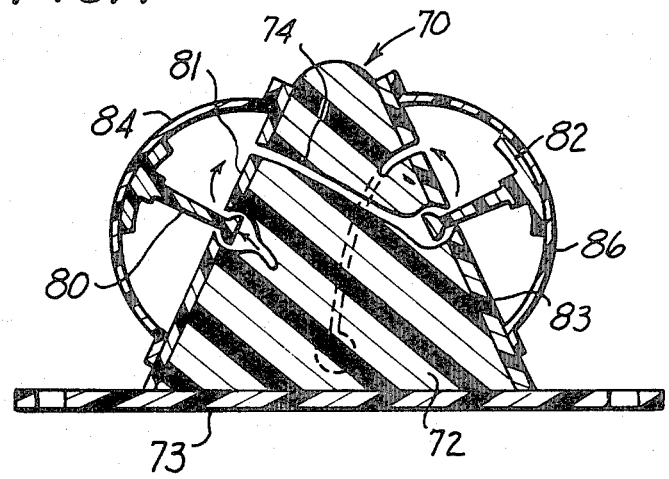
FIG. 7 is a side elevational view in cross section of an embodiment of a positive off valve.
Figure 8:
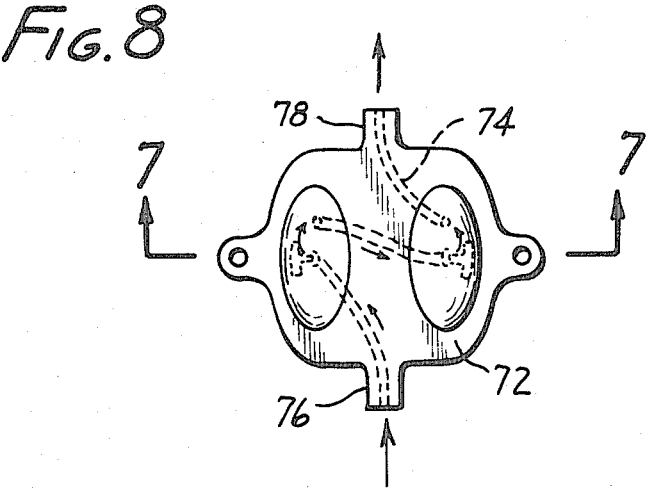
FIG. 8 is a top plan view of the positive off valve shown in FIG. 7.

A working embodiment of a positive off valve is disclosed in FIGS. 7 and 8. A positive off valve 70 has a body 72 and a base 73. The body of the positive off valve is constructed of an elastomeric material, such as silicone rubber. Extending through the body is a fluid-flow passageway 74. The fluid-flow passageway 74 connects to an inlet 76 and an outlet 78.

Along the fluid-flow passageway 74 is a first valve 80. The first valve 80 is provided a valve seat 81.

Also along the fluid-flow passageway 74 is a second valve 82. The second valve 82 is also provided with a valve seat 83.

Extending around the first valve 80 is a first resilient dome 84. Upon application of an external force to the first resilient dome 84, the first valve can be actuated to open the fluid-flow passageway to fluid flow. Preferably, the first valve is attached to the first resilient dome.

Extending around the second valve 82 is a second resilient dome 86. The second resilient dome is preferably attached to the second valve such that the second valve is maintained in its valve seat. Upon application of an external pressure to the second resilient dome, the second valve is unseated, opening the fluid-flow passageway to fluid flow. By using two valves in the positive off valve, fluid flow through the valve is only possible upon opening both the first and second valves. In such an arrangement, inadvertent flow of medication through the valve is avoided. Fluid can only pass through the valve when both of the resilient domes are depressed. In addition, increased fluid pressure upstream of the valve increases the seal of the first and second valves in the positive off valve, thereby preventing backflow through the valve.

The anti-reflux catheter 26 can be any suitable catheter depending upon the ailment of the patient, the location in which the catheter is to be implanted, and the medication to be administered. For example, the anti-reflux catheter can be a peritoneal catheter. The catheter can have provided openings, such as slit openings, which open only upon a predetermined fluid pressure being achieved within the catheter or the catheter can be provided with openings which remain open.

Figure 6:
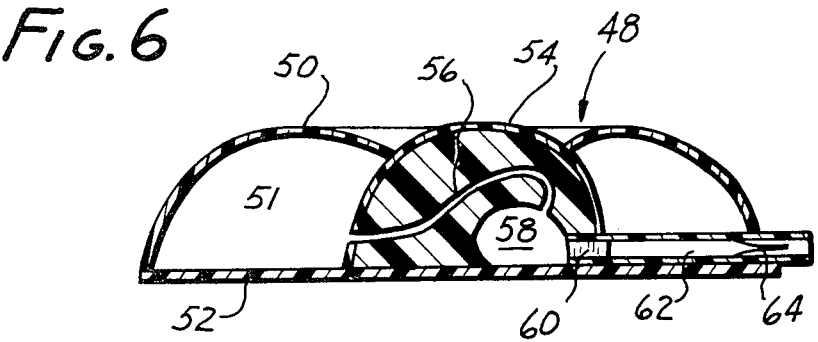
FIG. 6 is a side elevational view in cross section of another embodiment of a metering valve useful in the implantable metered dose drug delivery system herein.

Another embodiment of the metering valve is illustrated in FIG. 6. The metering valve 48 shown in FIG. 6 has a generally donut-shaped body 50 having a base 52. The metering valve 48 has an inner dome 54 which is generally constructed as the metering valve shown in FIGS. 2 and 4. That is, the dome is a resilient elastomer having a durometer of about 20 to 50. The inner dome has a fluid passageway 56 which can be collapsed as the fluid passageway 38 in the embodiment shown in FIGS. 2 and 4. Also within the inner dome is a dosing chamber 58. An outlet 62 leading from the chamber is provided with a first valve 60 and a second valve 64. The outlet, first valve, and second valve function as the outlet and first and second valves of the embodiment shown in FIGS. 2 and 4. To operate the metering valve 48 a force is applied on the dome 54 to occlude the fluid passageway, open the first valve and compress the chamber to force fluid out the outlet conduit.

The donut body 50 of the metering valve 48 extends circumferentially around the inner dome 54. The donut body 50 functions as a protector for the inner dome to protect the inner dome from being accidentally actuated. The donut body can extend to about the same height or higher than the dome portion of the metering valve. For example, when the patient may roll over and inadvertently push against the metering valve, the force is applied to the entire metering valve and does not contact the inner dome with sufficient force so as to actuate delivery of any medication.

The donut body 50 can be a solid material, such as a resilient elastomer to protect the inner dome or the donut body can be a chambered body which can function as a reservoir or injection site for the medication to be administered. For example, the donut body can contain a chamber 51 which is in fluid communication with the fluid passageway 56. The medication to be administered can then be drawn from the reservoir 51 within the donut body as is needed.

To operate the embodiment of FIG. 6, the patient can palpate the metering valve and locate the center dome. After locating the center dome, pressure can be exerted to deliver the measured dose of medication.

The implantable metered dose drug delivery system herein is capable of being totally implanted within the body of a patient. The system is capable of repeatedly delivering a measured dose of a medication, such as a pain reliever, directly to the nervous system or locus of the pain. The system is readily and simply actuated by the patient or by a physician attending the patient. By implanting the implantable metered dose drug delivery system herein, a patient can resume a somewhat normal life free of pain without the drawbacks normally associated with treatment of severe cancer pain, such as drowsiness and inactivity. The system has utility in the long term localized or systemic delivery of measured doses of drugs or agents in the treatment of local or systemic diseases or abnormalities and in the introduction of localized or systemic analgesic or hormonal agents.

We claim:

1. An implantable metered dose drug delivery system comprising:
   a puncturable and resealable injection site for providing an access to the system;
   a reservoir in fluid-flow communication with the injection site;
   a metering valve means in fluid-flow communication with the reservoir for measuring and storing a dosage amount of a drug to be administered and delivering the drug in dosage amounts upon external actuation, the metering valve means comprising a base, a resilient elastomeric solid body attached to the base, which resilient elastomeric solid body defines a chamber and a fluid passageway extending along its entire length within the resilient elastomeric solid body and which fluid passageway is in fluid communication with the chamber and deformable upon application of an external pressure applied to the resilient elastomeric solid body, an inlet conduit attached to the resilient elastomeric solid body in fluid-flow communication with the fluid passageway, an outlet conduit attached to the resilient elastomeric solid body in fluid-flow communication with the chamber, and a one-way valve means provided within the outlet conduit for opening and providing fluid flow from the chamber through the outlet conduit upon an external pressure being applied against the resilient elastomeric solid body, which external pressure collapses the fluid passageway occluding the fluid passageway to fluid flow and concomitantly collapses the chamber expelling any drug in the chamber from the chamber; and
   a delivery catheter fluid-flow communication with the metering valve means for delivering the drug dosage to the body.

2. An implantable metered dose drug delivery system as recited in claim 1 wherein the fluid passageway extends within the resilient elastomeric body of the metering valve in a superior position to the chamber such that upon application of an external force to the body of the metering valve the fluid passageway collapses occluding fluid flow through the fluid passageway.

3. An implantable metered dose drug delivery system as recited in claim 1 wherein the outlet conduit comprises a resilient elastomeric material having a greater durometer than the durometer of the elastomeric material of the resilient body.

4. An implantable metered dose drug delivery system as recited in claim 1 wherein the one-way valve means within the outlet conduit comprises a miter valve having an opening slit extending at right angles to the base of the metering valve.

5. An implantable metered dose drug delivery system as recited in claim 1 wherein the one-way valve means in the outlet conduit comprises a miter valve having a slit opening extending at right angles to the base and resilient elastomeric material extending around the miter valve in the outlet conduit.

6. An implantable metered dose drug delivery system as recited in claim 1 further comprising valve means for preventing fluid flow from the delivery catheter to the metering valve.

7. An implantable metered dose drug delivery system as recited in claim 6 wherein the valve means comprises a one-way valve positioned in the outlet conduit of the metering valve.

8. An implantable metered dose drug delivery system as recited in claim 1 wherein the solid body of the metering valve comprises a resilient elastomeric material having a durometer of about 20 to about 50 Shore A.

9. An implantable metered dose drug delivery system as recited in claim 8 wherein the outlet conduit comprises a resilient elastomeric material having a durometer greater than 50 Shore A.

10. An implantable metered dose drug delivery system as recited in claim 1 wherein the resilient elastomeric solid body of the metering valve means further comprises:
    a dome-shaped solid elastomeric body member; and
    a protective body member extending around the dome-shaped solid elastomeric body member.

11. An implantable metered dose drug delivery system as recited in claim 10 wherein the protective body member comprises a reservoir which is in fluid-flow communication with the fluid passageway extending within the domed body member.

12. An implantable metering valve for delivering dose amounts of a drug to the body, comprising:
    a resilient, deformable solid body member having a wall, a base, a chamber and a fluid passageway defined by and extending within said wall and which fluid passageway is in communication with the chamber, the chamber and fluid passageway being deformable upon application of an external compressive force applied to the resilient, deformable solid body member;
    an inlet conduit attached to the resilient, deformable solid body member and in communication with the fluid passageway;
    an outlet conduit attached to the resilient, deformable solid body member and in communication with the chamber; and
    one-way valve means in the outlet conduit which opens to provide fluid flow from the chamber through the outlet conduit upon application of an external force to the resilient, deformable solid body member for delivering dose amounts of a drug in the chamber.

13. An implantable metering valve as recited in claim 12 wherein the fluid passageway extends within said wall in a superior position to the chamber such that upon application of an external force to the resilient, deformable solid body member the fluid passageway collapses occluding fluid flow through the fluid passageway.

14. An implantable metering valve as recited in claim 12 wherein the outlet conduit comprises a resilient elastomeric material having a greater durometer than the durometer of the elastomeric material of the resilient solid body member.

15. An implantable metering valve as recited in claim 12 wherein the one-way valve means within the outlet conduit comprises a miter valve having an opening slit extending at right angles to the base of the metering valve.

16. An implantable metering valve as recited in claim 12 wherein the one-way valve means in the outlet conduit comprises a miter valve having a slit opening extending at right angles to the base and resilient elastomeric material extending around the valve in the outlet conduit.

17. An implantable metering valve as recited in claim 12 wherein the body of the metering valve comprises a resilient elastomeric material having a durometer of about 20 to 50 Shore A.

18. An implantable metering valve as recited in claim 12 wherein the outlet conduit comprises a resilient elastomeric material having a durometer greater than 50 Shore A.

19. An implantable metering valve as recited in claim 12 further comprising a protective body member extending around the resilient solid body member.

20. An implantable metering valve as recited in claim 19 wherein the protective body comprises a reservoir which is in fluid-flow communication with the fluid passageway extending within said wall.

21. An implantable metering valve as recited in claim 19 wherein the protective body member has a height above the base at least about equal to the height above the base of the resilient solid body member.

22. An implantable metering valve for delivering dose amounts of a drug to the body, comprising:
a resilient solid body member having a base a chamber and a fluid passageway defined by and extending within the solid body member in a superior condition to the chamber and which fluid passageway is in fluid communication with the chamber, the chamber and fluid passageway being deformable upon application of an external compressive force applied to the resilient, deformable solid body member,
an inlet conduit attached to the body member and in fluid communication with the fluid passageway;
an outlet conduit attached to the body member and in fluid communication with the chamber; and
a miter valve in the outlet conduit, which miter valve has its slit opening extending generally perpendicular to the base of the resilient body member and which slit opening is directed to and proximal to the chamber such that upon application of an external force to the resilient body member the miter valve opens for delivering dose amounts of a drug in the chamber through the outlet conduit.

23. An implantable metering valve as recited in claim 22 further comprising elastomeric material positioned around the miter valve in the outlet conduit.

* * * * *

UNITED STATES PATENT AND TRADEMARK OFFICE
CERTIFICATE OF CORRECTION

PATENT NO. : 4,544,371

DATED : October 1, 1985

INVENTOR(S) : Ray H. Dormandy, Jr. and Frederick L. Coe

It is certified that error appears in the above-identified patent and that said Letters Patent are hereby corrected as shown below:

Column 10, line 9, after "base" insert -- , --.

Column 10, line 12, change "condition" to -- position --.

Column 10, line 17, after "member" change the "," to -- ; --.

Signed and Sealed this

Seventeenth Day of December 1985

[SEAL]

Attest:

DONALD J. QUIGG

Attesting Officer

Commissioner of Patents and Trademarks